United States Patent [19]

Shirasaka

[11] Patent Number: 4,554,926

[45] Date of Patent: Nov. 26, 1985

[54] ULTRASONIC PULSE DOPPLER BLOOD FLOW METER WITH PROVISION TO CREATE ULTRASONIC TEST WAVES WHICH, WHEN REFLECTED FROM A STATIONARY OBJECT, RESULT IN ECHOES SIMILAR TO THOSE PRODUCED BY A MOVING OBJECT

[75] Inventor: Toshio Shirasaka, Tochigi, Japan

[73] Assignee: Tokyo Shibaura Denki Kabushiki Kaisha, Kawasaki, Japan

[21] Appl. No.: 430,003

[22] Filed: Sep. 30, 1982

[30] Foreign Application Priority Data

Oct. 23, 1981 [JP] Japan .................. 56-168644

[51] Int. Cl.⁴ ........................................... A61B 10/00
[52] U.S. Cl. ................................................. 128/663
[58] Field of Search .................... 128/663, 90; 367/13; 73/861.25

[56] References Cited

U.S. PATENT DOCUMENTS

| | | | |
|---|---|---|---|
| 4,250,634 | 2/1981 | Buckler | 367/13 X |
| 4,255,977 | 3/1981 | Newhouse et al. | 128/663 X |
| 4,265,126 | 5/1981 | Papadofrangakis | 73/861.25 |
| 4,407,293 | 10/1983 | Suarez, Jr. et al. | 128/663 X |

OTHER PUBLICATIONS

The Doppler Signal Simulator for Ultrasonic Pulsed Doppler System, Shirasaka et al., Apr. 1981, p. 156.
Baker D. W., "Pulsed Doppler Blood Flow Sensing" IEEE Trans. on Sonics & UTS, vol. SU17, No. 3, Jul. 1970.

Primary Examiner—Kyle L. Howell
Assistant Examiner—Francis J. Jaworski
Attorney, Agent, or Firm—Cushman, Darby & Cushman

[57] ABSTRACT

An ultrasonic pulse Doppler blood flow meter which has:

a rate pulse generator for outputting a rate pulse, a pulser receiving the rate pulse for outputting a drive pulse, a transducer excited by the drive pulse for transmitting an ultrasonic wave into an object to be detected and receiving the echoes thereof for converting the echoes into an electrical signal, a range gate circuit for outputting a sampling pulse after a predetermined time from the output of the rate pulse, a sample and hold circuit for sampling and holding the echo signals from the transducer in accordance with the sampling pulse, a converter for Fourier-converting the sampled echo signals, and a monitor for indicating in a intensity the converted echo signals advantageously further comprising:

shifting circuit for shifting said predetermined time between the rate pulse and the range gate pulse at the individual periods of the rate pulse, and a switch circuit for selectively connecting the rate pulse generator and the shifting circuit to the drive pulse generator.

5 Claims, 18 Drawing Figures

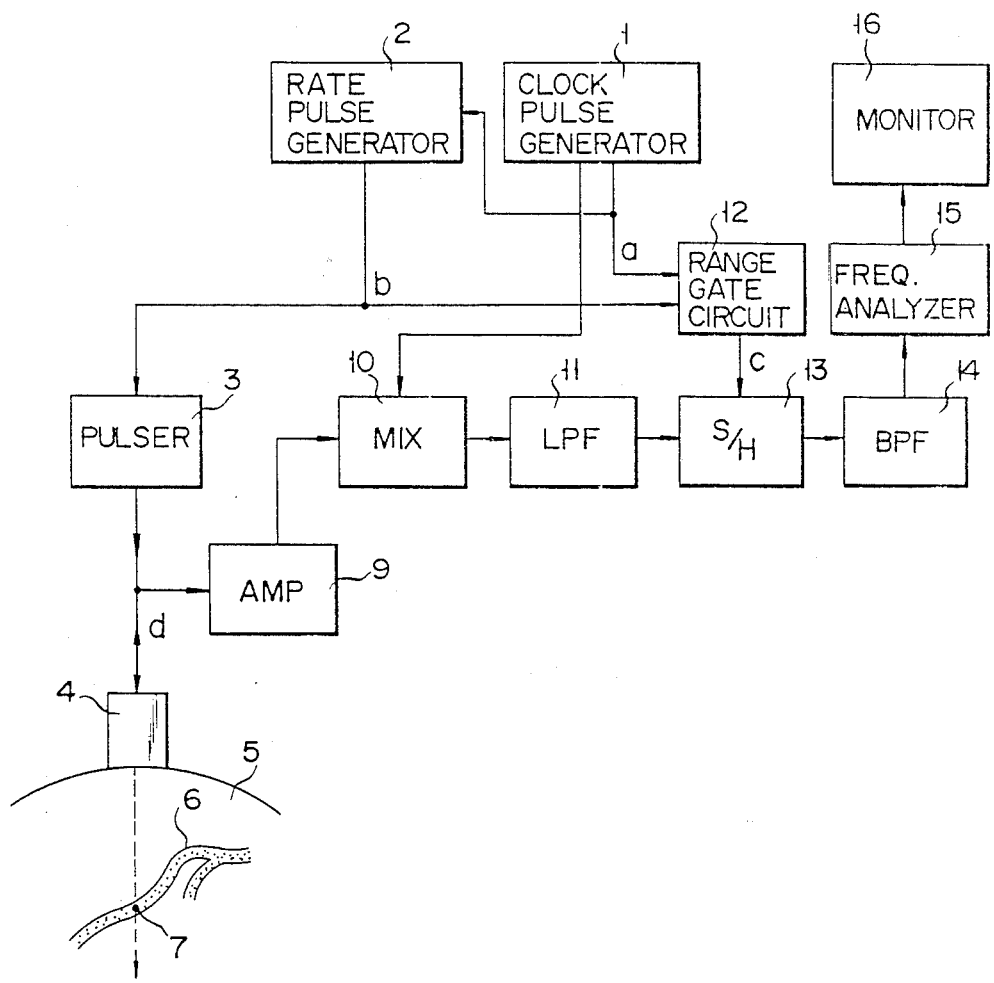
FIG. 1 (PRIOR ART)
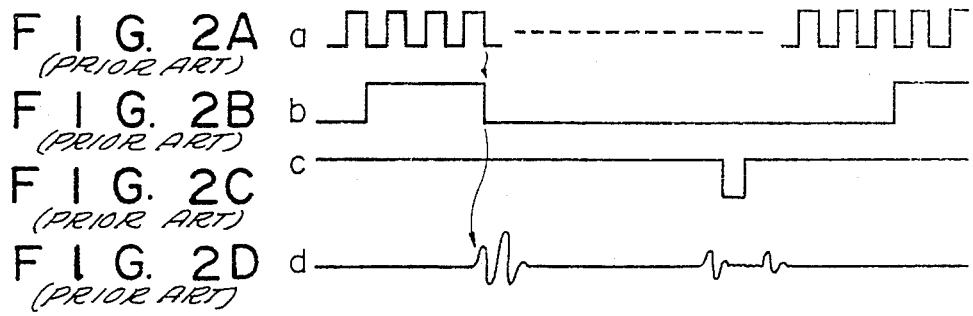
FIG. 2A (PRIOR ART)
FIG. 2B (PRIOR ART)
FIG. 2C (PRIOR ART)
FIG. 2D (PRIOR ART)

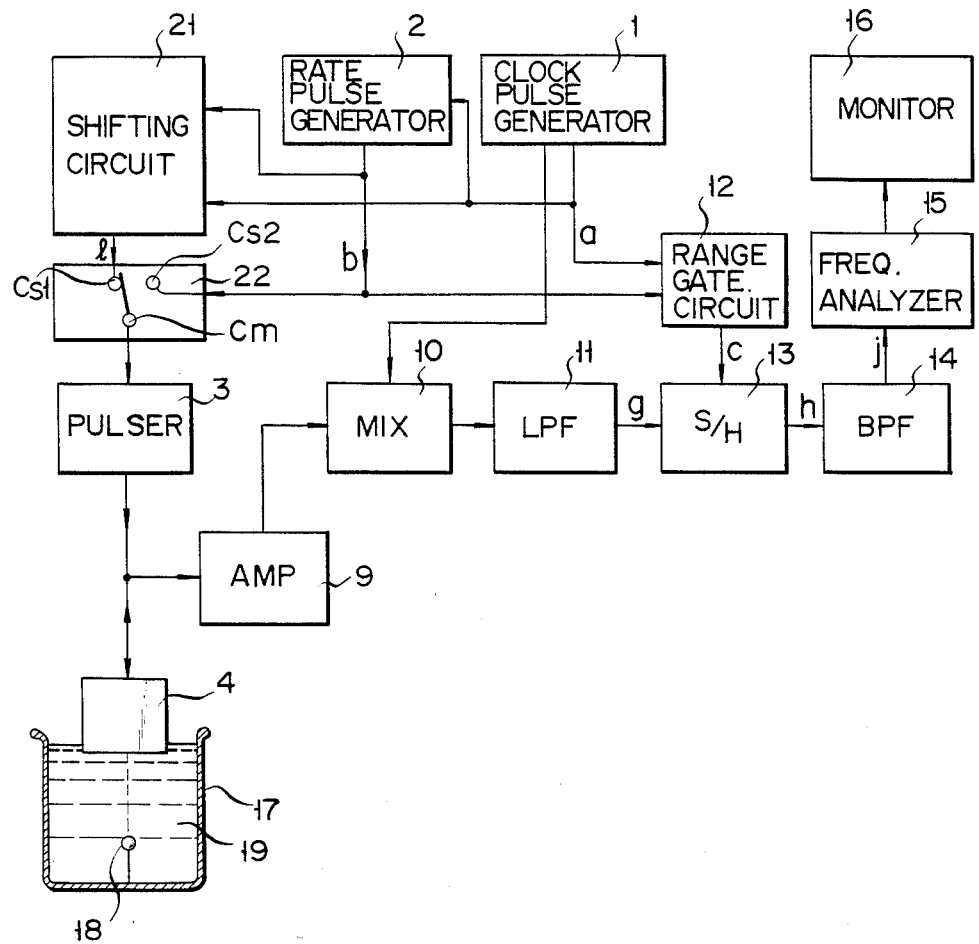
FIG. 3
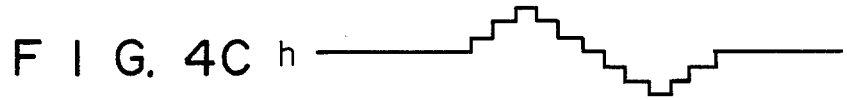
FIG. 4C h
FIG. 4D i

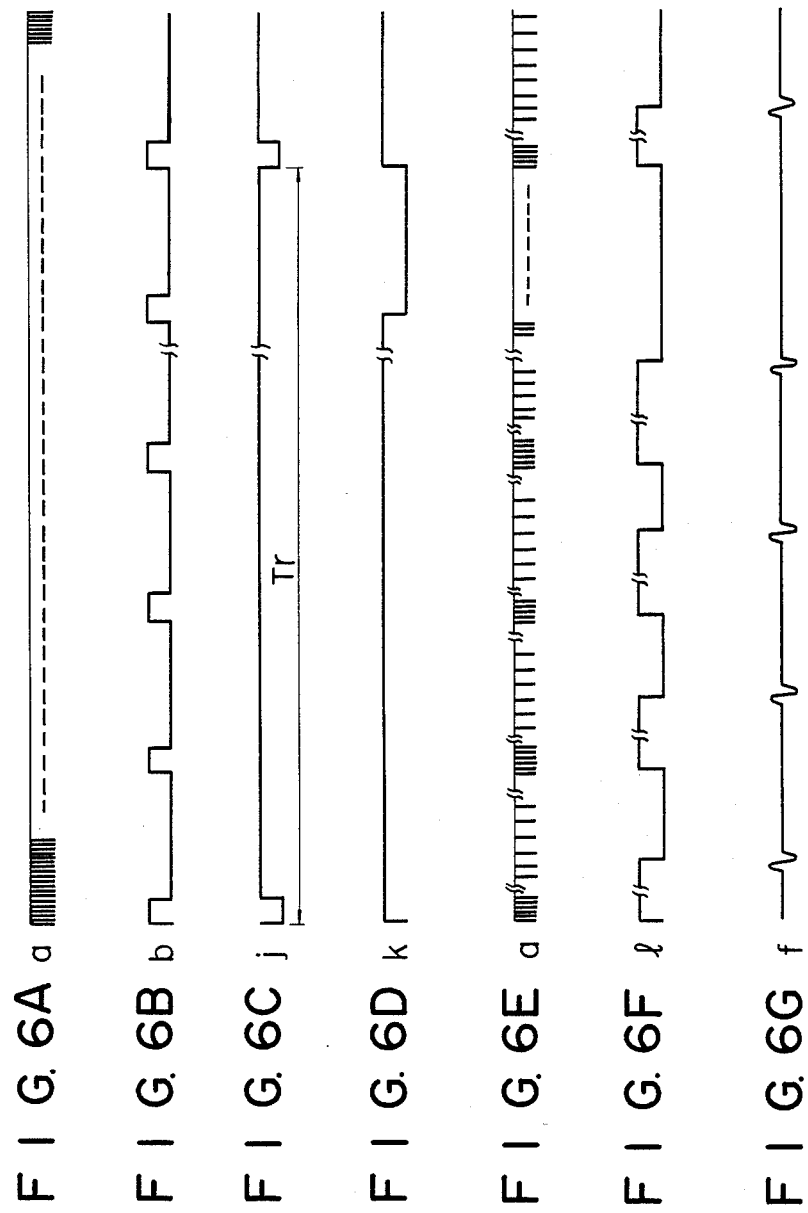

ULTRASONIC PULSE DOPPLER BLOOD FLOW METER WITH PROVISION TO CREATE ULTRASONIC TEST WAVES WHICH, WHEN REFLECTED FROM A STATIONARY OBJECT, RESULT IN ECHOES SIMILAR TO THOSE PRODUCED BY A MOVING OBJECT

BACKGROUND OF THE INVENTION

The present invention relates to an ultrasonic pulse Doppler blood flow meter which is associated with an operation checking mechanism.

An ultrasonic pulse Doppler blood flow meter serves to transmit by an ultrasonic transducer an ultrasonic wave into the body, receive its echoes, extract only echoes from a blood flow corpuscle or cell at the position to be measured of the received echoes, obtain a Doppler frequency shift from the extracted echoes, and perform a spectrum analysis on the echoes, thereby obtaining the blood flow velocity. More specifically, the Doppler frequency shift fd can be expressed by the following equation:

$$fd = [(2V \cdot \cos \theta)/C] \cdot fc \quad (1)$$

where
- $V$: the flow velocity of corpuscle (i.e., blood flow velocity),
- $\theta$: the angle between the direction of the ultrasonic beam and the direction of the blood flow,
- $C$: velocity of sound in tissue
- $fc$: the central frequency of the ultrasonic wave transmitted.

From the equation (1), it is understood that the flow velocity V of the blood is proportional to the Doppler frequency shift fd. The Doppler blood flow meter obtains the blood flow velocity V in view of this relation by obtaining the Doppler frequency shift of the echoes of the blood corpuscle.

An example of a conventional such flow meter is shown in FIG. 1. FIGS. 2A to 2D are time charts of the waveforms of the signals in the respective sections of the flow meter shown in FIG. 1. A clock pulse a (FIG. 2A) of a predetermined frequency is produced from a clock pulse generator 1. A rate pulse generator 2 receives the clock pulse a from the clock pulse generator 1 and produces a rate pulse b (FIG. 2B) of the period corresponding to the period of the ultrasonic wave (the driven period of an ultrasonic transducer 4). The rate pulse b is applied to a pulser 3 and a range gate circuit 12. The pulser 3 drives the transducer 4 in synchronization with the fall of the rate pulse b. When the transducer 4 is driven, the transducer 4 transmits an ultrasonic wave into a living body 5. The ultrasonic wave propagates in the living body 5 and is reflected on a vascular wall 6 or blood corpuscles or cells (in FIG. 1, only the blood corpulscle designated) by reference numeral 7 is indicated by a thick black point, and other blood corpuscles are indicated by small points). The echoes d are received by the transducer 4, which converts the echoes into an electric signal of the magnitude corresponding to the intensity of the echoes. The converted echo signals are inputted to a preamplifier AMP 9, and are amplified to the suitable amplitude. The amplified echo signals are then inputted to a mixer MIX 10. To the MIX 10 is inputted a reference signal of the frequency corresponding to the central frequency of the ultrasonic wave transmitted from the transducer 4, from the clock pulse generator 1. The echo signals are mixed by th MIX 10 with the reference signal from the generator 1. The mixed signal is in turn inputted to a low pass filter LPF 11, which removes the harmonic component of the mixed signal. The echo signals thus fed through the low pass filter LPF 11 are in turn inputted to a sample & hold (S/H) circuit 13, which samples only the echo signals from the position to be measured in accordance with the range gate pulse from the range gate circuit 12 as a sampling signal. The echo signals sampled are held at the S/H circuit 13 until the S/H circuit 13 receives the next range gate pulse. The echo signals sampled are in turn inputted to a band pass filter BPF 14, which removes the harmonic wave components produced by sampling, echo from a stationary reflector such as a vascular wall, and Doppler frequency shift signals from a moving article moving relatively slowly to thus sample only the Doppler frequency shift signals due to the blood flow. The echo signals from the band pass filter BPF 14 are then inputted to a frequency analyzer 15, which is composed, for example, of an FFT (fast fourier transformer), and which frequency-analyzes the echo signals to produce a frequency spectrum corresponding to a blood flow signal. The frequency spectrum from the band pass filter BPE 14 is in turn inputted to a monitor 16, which then indicates as an intensity a blood flow signal.

Blood flow information is obtained by the conventional blood flow meter shown in FIG. 1 by the above-described operation.

Since the conventional ultrasonic pulse Doppler blood flow meter however produces the blood flow information in the format of frequency (Doppler frequency shift) as described above, its circuit arrangement is complicated, and checks for the operation of the flow meter is accordingly complicated. As a conventional operation checking device, there is known "The Doppler Signal Simulator for Ultrasonic Pulsed Doppler System" described on Japan Ultrasonic Medical Society, Bulletin, 38-C-24 issued in April, 1981. This simulator employs as an echo signal obtained from a moving article an electric sinusoidal burst signal and obtains a Doppler frequency shift by varying the phase of the burst signal.

Since the burst signal thus obtained is not however an actual echo, this device cannot generally check together with the characteristics of the ultrasound field and the transmitting & receiving circuits according to a transducer.

SUMMARY OF THE INVENTION

It is an object of the present invention to provide an ultrasonic pulse Doppler blood flow meter which is capable of readily performing the operation check thereof in view of the aforementioned drawbacks of the conventional flow meter.

According to the invention, these is provided an ultrasonic pulse Doppler blood flow meter comprising:
rate pulse generating means for producing a rate pulse of a predetermined repetition period,
drive pulse generating means responsive to the rate pulse for producing a drive pulse,
transducer means responsive to the drive pulse for transmitting an ultrasonic wave into an object to be detected and responsive to the echoes thereof for converting the received echoes into an electrical signal, range gate circuit means for producing a range gate pulse after a predetermined time from the rate pulse, sampling means responsive to the range gate pulse for sampling only echo signals from a predetermined depth of the received echo signals, frequency analyzing means for performing the frequency analyzation of the sampled echo signals, display means for indicating in an intensity the analyzed signals, shifting circuit means for shifting a predetermined time between the rate pulse and the range gate pulse by a predetermined time at every individual period of the rate pulse, and switching means for selectively connecting said rate pulse generating means and said shifting circuit means to said drive pulse generating means.

According to the invention, there is further provided an ultrasonic pulse Doppler blood flow meter comprising:

rate pulse generating means for producing a rate pulse of a predetermined repetition period, drive pulse generating means responsive to the rate pulse for producing a drive pulse, transducer means responsive to the drive pulse for transmitting an ultrasonic wave into an object to be detected and responsive to the echoes thereof for converting the received echoes into an electrical signal, range gate circuit means for producing a range gate pulse after a predetermined time from the rate pulse, sampling means responsive to the range gate pulse for sampling only echo signals from a predetermined depth of the received echo signals, frequency analyzing means for performing the frequency analyzation of the sampled echo signals, display means for indicating in an intensity the analyzed signals, shifting circuit means for shifting the rate pulse by a predetermined time at every individual period, thereby shifting said predetermined time between the rate pulse and the range gate pulse by a predetermined time at every individual period of the rate pulse, and switching means for selectively connecting said rate pulse generating means and said shifting circuit means to said drive pulse generating means.

According to the invention, there is further provided an ultrasonic pulse Doppler blood flow meter comprising:

rate pulse generating means for producing a rate pulse of a predetermined repetition period, drive pulse generating means responsive to the rate pulse for producing a drive pulse, transducer means responsive to the drive pulse for transmitting an ultrasonic wave into an object to be detected and responsive to the echoes thereof for converting the received echoes into an electrical signal, range gate circuit means for producing a range gate pulse after a predetermined time from the rate pulse, sampling means responsive to the range gate pulse for sampling only echo signals from a predetermined depth of the received echo signals, frequency analyzing means for performing the frequency analyzation of the sampled echo signals, display means for indicating in an intensity the analyzed signals, shifting circuit means for shifting the range gate pulse by a predetermined time at every individual period, thereby shifting said predetermined time between the rate pulse and the range gate pulse by a predetermined time at every individual period of the rate pulse, and switching means for selectively connecting said rate pulse generating means and said shifting circuit means to said drive pulse generating means.

According to the invention, there is still further provided a quasi Doppler signal generating apparatus comprising:

rate pulse generating means for producing a rate pulse of a predetermined repetition period, range gate circuit means for producing a range gate pulse by delaying in a predetermined time from the rate pulse, shifting circuit means for shifting a predetermined time between the rate pulse and the range gate pulse by a predetermined time at individual period of the rated pulse, drive pulse generating means responsive to the output pulse from said shifting means for producing a drive signal, transducer means responsive to the drive pulse for transmitting an ultrasonic wave into an object to be detected and responsive to the echoes thereof for converting the echoes into an electrical signal, sampling means for sampling only the echo signals from a predetermined depth of the received echo signals in accordance with the range gate pulse, frequency analyzing means for performing the frequency analyzation of the sampled echo signals, and display means for indicating in an intensity the analyzed signals.

According to the invention, there is further provided a quasi Doppler signal generating apparatus comprising:

rate pulse generating means for producing a rate pulse of a predetermined repetition period, range gate circuit means for producing a range gate pulse by delaying in a predetermined time from the rate pulse, shifting circuit means for shifting the rate pulse by a predetermined time at every individual period, thereby shifting said predetermined time between the rate pulse and the range gate pulse by a predetermined time at individual period of the rated pulse, drive pulse generating means responsive to the output pulse from said shifting means for producing a drive signal, transducer means responsive to the drive pulse for transmitting an ultrasonic wave into an object to be detected and responsive to the echoes thereof for converting the echoes into an electrical signal, sampling means for sampling only the echo signals from a predetermined depth of the received echo signals in accordance with the range gate pulse, frequency analyzing means for performing the frequency analyzation of the sampled echo signals, and display means for indicating in an intensity the analyzed signals.

According to the invention, there is still further provided a quasi Doppler signal generating apparatus comprising:

rate pulse generating means for producing a rate pulse of a predetermined repetition period, range gate circuit means for producing a range gate pulse by delaying in a predetermined time from the rate pulse, shifting circuit means for shifting the range gate pulse by a predetermined time at every individual period, thereby shifting said predetermined time between the rate pulse and the range gate pulse by a predetermined time at individual period of the rated pulse, drive pulse generating means responsive to the output pulse from said shifting means for producing a drive signal, transducer means responsive to the drive pulse for transmitting an ultrasonic wave into an object to be detected and responsive to the echoes thereof for converting the echoes into an electrical signal, sampling means for sampling only the echo signals from a predetermined depth of the received echo signals in accordance with the range gate pulse, frequency analyzing means for performing the frequency analyzation of the sampled echo signals, and display means for indicating in an intensity the analyzed signals.

BRIEF DESCRIPTION OF THE DRAWINGS

FIG. 1 is a block circuit diagram of an example of a conventional ultrasonic pulse Doppler blood flow meter;

FIGS. 2A to 2D are timing charts of the signals at the respective sections of the blood flow meter shown in FIG. 1;

FIG. 3 is a block circuit diagram of an embodiment of an ultrasonic pulse Doppler blood flow meter according to the present invention;

FIGS. 4A to 4D are timing charts of the signals of the respective sections of the blood flow meter shown in FIG. 3;

FIGS. 6A to 6G are timing charts of the signals of the respective sections of the shifting pulse generator in FIG. 5.

DETAILED DESCRIPTION OF THE PREFERRED EMBODIMENTS

The principle of the present invention will be first described. When an ultrasonic wave is transmitted from a transducer through a body to a blood corpuscle moving at a velocity V in the direction of the beam of the ultrasonic wave in a period Tr in a repeated manner, the time required from the transmission of the ultrasonic wave through the arrival of the wave at the blood corpuscle to the reception of the wave by the transducer sequentially becomes different for the respective waves transmitted successively.

Assume that the above-described required time for a certain arbitrary transmission of the ultrasonic wave is t and that the distance of the transducer to the blood corpuscle at the time when the ultrasonic wave transmitted from the transducer arrives at the blood corpuscle is x. Because a velocity of the blood flow (blood corpuscle etc.) is generally lower than a propagation velocity, S of the ultrasonic wave, the required time t can be obtained from the following equation:

$$t \approx 2x/S \quad (2)$$

The required time t' of the next transmitted ultrasonic wave (the transmitted wave after a period Tr from the previously transmitted wave) can be obtained from the following equation, since the blood corpuscle has moved in the distance of $\Delta x \; (=V \cdot Tr)$ during one period Tr:

$$t' \approx 2(x+\Delta x)/S \quad (3)$$

Assume that $t'-t=\Delta t$ is set, $$\Delta t \approx 2\Delta x/S \quad (4)$$

$$\approx 2V \cdot Tr/S$$

can be obtained.

Let us now relate this teaching concerning blood corpuscles flowing through the body to a testing situation in which a stationary target is employed.

The equation (4) is substituted for the equation (1), and $\theta=0$ is set (which is reasonable in a testing situation with a transducer aimed at a stationary target), and the equation (1) can be transformed as follows:

$$fd \approx \Delta t \cdot fc/Tr \quad (5)$$

As evident from the equation (5), the $\Delta t$ becomes a factor for determining the Doppler frequency shift fd. In view of the relationship between the fd and $\Delta t$, it is understood that a quasi Doppler frequency shift fd can be obtained by shifting by $\Delta t$ the time interval between the rate pulse and the range gate pulse for each transmitted wave (i.e., for each transmission period). Thus, Doppler shift can be created in vitro, using reflections from a stationary target by the $\Delta t$ shifting as well as in vivo using reflections from moving corpuscles. This effect is used in the present invention to simulate dopper shift caused by blood flow using a stationary target in vitro.

An embodiment of the blood flow meter according to the present invention will now be described in more detail with reference to the accompanying drawings and particularly to FIG. 3.

Figure 4B:
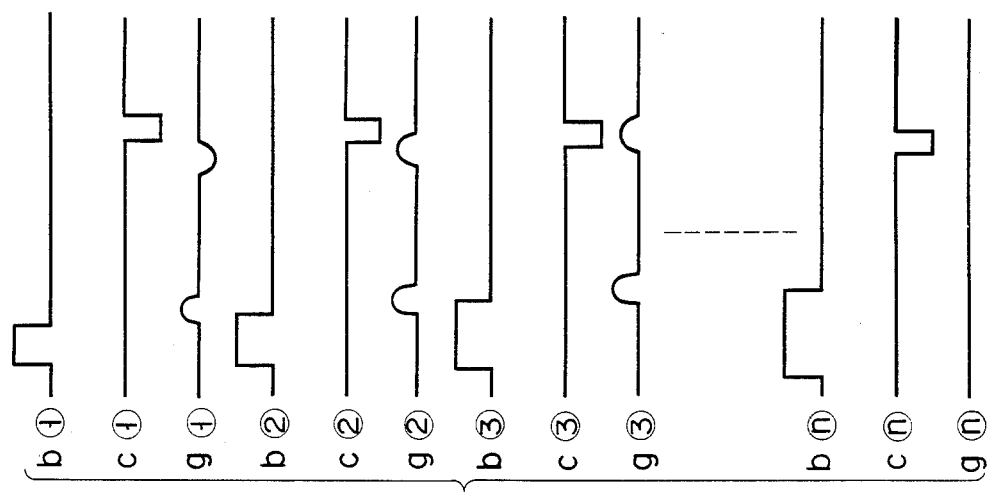
Figure 4A:
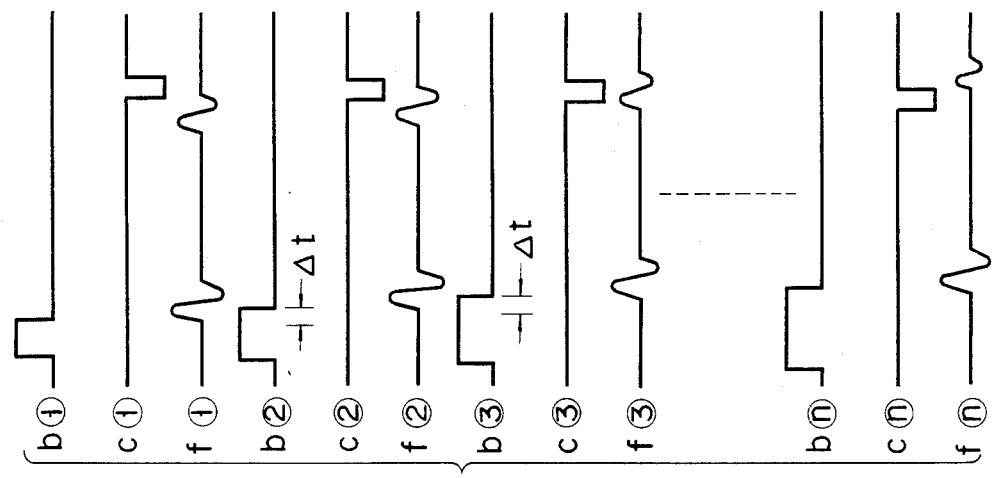

A clock pulse generator 1 generates a clock pulse a (e.g., 19.2 MHz) (FIG. 2A) of a predetermined period. The clock pulse generator 1 is connected to rate pulse generator 2. The rate pulse generator 2 frequency-divides the clock pulse thus received from the generator 1 and produces a rat pule b (FIG. 2B) of a suitable frequency. The frequency of the rate pulse corresponds to the frequency for driving the ultrasonic transducer. The rate pulse generator 2 is connected to a shifting circuit 21, and the rate pulse from the generator 2 is inputted to the shifting circuit 21. The shifting circuit 21 also receives a clock pulse from the clock pulse generator 2 in addition to the rate pulse from the rate pulse generator 2. Thus, the shifting circuit 21 produces pulses b(1), b(2), . . . , b(n) (FIGS. 4A and 4B) having increased pulse width sequentially in the amount of the time $\Delta t$ for each rate pulse b in accordance with the rate pulse b and the clock pulse a. The shifting circuit 21 is connected to a switch circuit 22. The switch circuit 22 has two stationary contacts CS1, CS2 and a movable contact Cm. The circuit 21 is connected to the stationary contact CS1. The rate pulse generator 2 is connected to the stationary contact CS2. A pulser 3 is connected to the movable contact Cm. The switch circuit 22 serves to select the device as the operation of the circuit for the original blood flow sensing or as the circuit for detecting the quasi Doppler frequency shift for the check. When the device is set to the blood flow sensing mode, the movable contact Cm is connected to the stationary contact CS2 side, while when the device is set to the check mode, the movable contact Cm is connected to the stationary contact CS1 side. The operation of the circuit in the case of the sensing mode is substantially similar to that of the conventional blood flow meter described previously with reference to FIG. 1.

In other words, the clock pulse signal a (FIG. 2A) of a predetermined frequency such as for example, 19.2 MHz is provided by the clock pulse generator 1. The rate pulse generator 2 frequency-divides the clock pulse a thus received from the generator 1 and produces a rate pulse b (FIG. 2B) of the period corresponding to the period of the transmitted ultrasonic wave (the driven period of the ultrasonic transducer 4). The rate pulse b is in turn supplied to a pulser 3 and a range gate circuit 12. The pulser 3 drives the transducer 4 in synchronization with the fall of the rate pulse b. The transducer 4, thus driven, transmits an ultrasonic wave into a living body. The wave thus transmitted propagates in the living body, and is reflected on the vascular wall, blood corpuscles. The echoes d (FIG. 2D) are received by the transducer 4, which in turn converts the received echoes into an electric signal of the magnitude corresponding to the intensity of the echoes. The converted echo signals are inputted to the pre-amplifier AMP 9, which in turn amplifies the inputted signals to a suitable amplitude. The amplified echo signals are then inputted to a mixer MIX 10. To the MIX 10 is inputted the reference signal of the frequency corresponding to the central frequency of the ultrasonic wave transmitted from the transducer 4, from the clock pulse generator 1. The MIX 10 then mixes the echo signals with the reference signal. The mixed signal is in turn inputted to a low pass filter LPF 11 which then removes the harmonic wave components from the mixed signal. The echo signals thus fed through the low pass filter LPF 11 are in turn inputted to a sample & hold (S/H) circuit 13, which in turn samples only the echo signal from the position to be measured in accordance with the range gate pulse from the range gate circuit 12 as a sampling signal. The echo signals sampled are held at the S/H circuit 13 until the S/H circuit 13 receives the next range a gate pulse. The sampled echo signals are then inputted to a band pass filter BPF 14, which removes the harmonic wave components produced by sampling, echo from a stationary reflector such as vascular wall, and Doppler frequency shift signals from a moving article moving relatively slowly, and samples only the Doppler frequency shift signals due to the blood flow. The signal from the band pass filter is in turn inputted to a frequency analyzer 15, which is composed, for example, of an FFT (fast fourier transformer), which in turn frequency-analyzes the signal thus inputted and produces a frequency spectrum corresponding to a blood flow signal. The frequency spectrum from the frequency analyzer 15 is in turn inputted to a monitor 16, which indicates as a blood flow signal its intensity.

The blood flow can be detected similarly to the blood flow meter in FIG. 1 by the operation described above.

The operation of the blood flow meter in the case of check mode will now be described.

When the blood flow meter is set to the check mode, the pulses b(1), b(2), . . . , b(n) from the circuit 21 is inputted to the pulser 3. The pulser 3 outputs a drive pulse to the transducer 4 in accordance with the pulses b(1), b(2), . . . , b(n). The transducer 4 excites and transmits an ultrasonic wave at the fall of the drive pulse thus received. The transducer 4 is disposed at the water surface of water 19 filled in a water tank 17. A ball target 18 which functions as a reflecting article is disposed under water. The transducer 4 is excited by the drive pulse from the pulser 3 to transmit the ultrasonic wave. The ultrasnoic wave propagates in the water 19 to arrive at the target 18. The echoes from the target is received by the transducer 4. The echoes thus received are converted into an electric signal by the transducer 4. The electrical echo signal is then inputted to a preamplifier 9, and is amplified to a signal having a suitable amplitude. The amplifier 9 is connected to a mixer 10, and the amplified echo signals are in turn inputted to the mixer 10. To the mixer 10 is also inputted the reference signal from the clock pulse generator 1. The mixer 10 mixes the echo signals with the reference signal, thereby phase-detecting the echo signals. The mixer 10 is connected to a low pass filter 11, and the phase-detected echo signal $g(1), g(2), \ldots, g(n)$ (FIGS. 4A and 4B) are in turn inputted to a low pass filter 11. The harmonic wave components produced by the mixer 10 are removed by the low pass filter 11. The low pass filter 11 is connected to a sample & hold circuit 13, and the output echo signals from the low pass filter are in turn inputted to the sample & hold circuit 13. To the sample & hold circuit 13 is connected a range gate circuit 12. The range gate circuit 12, thus connected, receives the clock pulse from the clock pulse generator 1 and the rate pulse from the rate pulse generator 2, and outputs sample signal (range gate pule) $c(1), c(2), \ldots, c(n)$ for producing only the echo signals from a predetermined depth. The sample & hold circuit 13 samples and holds only the echo signals from the target 18 inputted from the low pass filter 11 in accordance with the sample signal from the range gate circuit 12. The sample and hold circuit 13 is connected to a band pass filter 14, and the sampled signal h (FIG. 4C) is inputted to the band pass filter 14. Only the signal component i (FIG. 4D) of the Doppler frequency shift, i.e., quasi Doppler frequency shift is produced from the blood flow by the band pass filter 14. The band pass filter 14 is connected to a frequency analyzer 15, and the signal from the filter 14 is in turn inputted to the frequency analyzer 15. The signal from the filter 14 is frequency-analyzed by the frequency analyzer 15. Thus, the frequency analyzation of the echo from the target 18 as a stationary article is performed. The frequency analyzer 15 is connected to a monitor 16 as a display device, and the monitor 16 indicates in an intensity the frequency-analyzed Doppler frequency shift on its screen. The $b(1), b(2), \ldots, b(n)$ are repeated at a predetermined period Ta. This repetition period TA has a predetermined relation with respect to the interval $\Delta f$ of the frequency spectrum having the Doppler frequency shift, i.e., $\Delta f = 1/Ta$. Accordingly, it is preferable to set the period Ta so that the interval $\Delta f$ becomes a freqency corresponding to the frequency resolution of the frequency analyzer 15.

Figure 5:
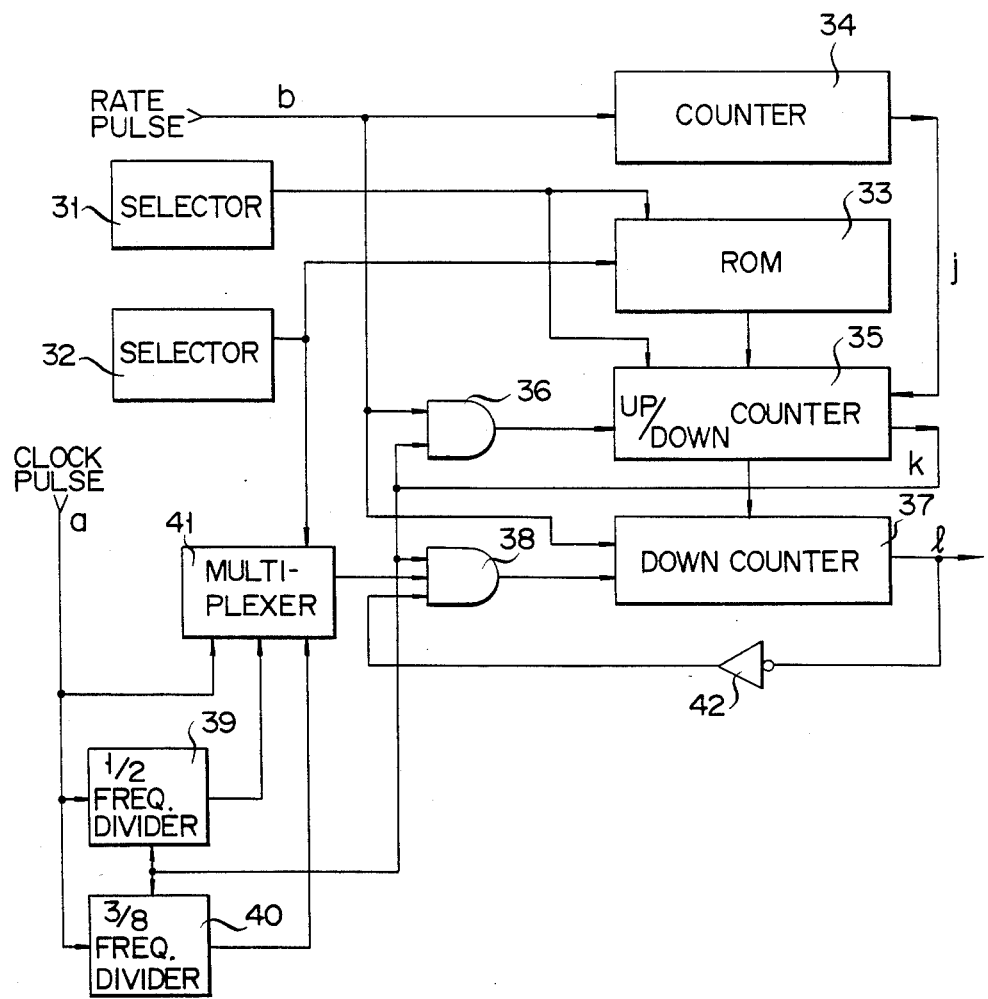
FIG. 5 is a block circuit diagram of an example of the shifting pulse generator associated with the blood flow meter in FIG. 1.

FIG. 5 shows a block circuit diagram of an example of the shifting pulse generator 21. FIGS. 6A to 6F are time charts of the signals of the respective sections of the generator 21.

A selector 31 is connected to a Read Only Memory (ROM) 33 and an UP/DOWN Counter 35 to switch the memory 33 and the UP/DOWN mode of the counter 35. The selector 31 switches the memory 33 and the counter 35 to the count up mode when signals are product to simulate the ball target 18 (reflector) moving toward the transducer 4 while switches the memory 33 and the counter 35 to the count down mode when signals are produced to simulate the target 18 moving away from the transducer 4. A selector 32 is connected to the ROM 33 and a multiplexer 41. The selector 32 sets a Doppler frequency shift fd to be obtained, and, more concretely, sets the Doppler frequency shift by supplying a 2-bit control a signal to the ROM 33 and the multiplexer 41. A counter 34 receives a rate pulse b (FIG. 6B) and outputs signal j when it counts a predetermined pieces of the pulses corresponding to the period Ta. A counter 34 is connected to the UP/DOWN counter 35, and the signal j is inputted to the UP/DOWN counter 35. A 2-input AND gate 36 receives at one input terminal a rate pulse b and is connected at the other input terminal to the output terminal of the UP/DOWN counter 35. The output terminal of the AND gate is connected to the input terminal of the UP/DOWN counter 35. The output terminal of the UP/DOWN counter 35 is connected to the first input terminal of a 3-input AND gate 38. A clock pulse (a) is respectively inputted to a ½-frequency divider 39 and ⅜-frequency divider 40. The output terminals of the dividers 39 and 40 are respectively connected to the multiplexer 41. Thus, the pulse signal divided into ½-frequency by the divider 39 and the pulse signal divided into ⅜-frequency by the divider by the divider 40 are respectively inputted to the multiplexer 41. A clock pulse a (FIG. 6A) is also inputted directly to the multiplexer 41. The output terminal of the UP/DOWN counter 35 is respectively connected to the dividers 39 and 40, and the output signal of the UP/DOWN counter 35 is inputted to the dividers 39 and 40. To the multiplexer 41 are inputted 2-bit control signal from the selector 32, and the multiplexer 41 selects one of the input pulse signals in accordance with the bit content of this control signal. The selected pulse signal is inputted to the second input terminal of the 3-input AND gate 38. The output terminal of the AND gate 38 is connected to the input terminal of a Down Counter 37. To the Down counter 37 is further inputted a rate pulse b. The output terminal of the Down counter 37 is connected as the output terminal of the shifting pulse generator 21 to the first stationary contact CS1 of the switching circuit 32, and is also connected to the input terminal of an inverter 42. The output terminal of the inverter 42 is connected to the third input terminal of the 3-input AND gate 38.

When the UP/DOWN counter 35 receives the signal j (FIG. 6C), the counter 35 latches, for example, 8-bit data of the ROM 33. Then, the counter 35 up-counts, for example, the data latched by the rate pulse b supplied through the gate 36. The counted value of the UP/DOWN counter 35 is inputted to the Down counter 37. When the bits forming the latched data such as 8 bits become all High level, the UP/DOWN counter 35 produces an output signal k (FIG. 6D) of Low level. This output signal k is inputted as a signal for closing the gate to the AND gates 36, 38, and the frequency dividers 40, 41. When the rate pulse b is inputted to the Down counter 37, the Down counter 37 latches, for example, 8 bits of the UP/DOWN counter 35. Then, the Down counter 37 downcounts the data selected by the multiplexer 41 and latched by the pulse signal inputted. When all bits of the latched data become Low level, the Down counter 37 produces a signal l of High level. The signal l (FIG. 6F) is inputted through the inverter 42 to the gate 38, and is also supplied as the output signal of the shifting pulse generator 21 to the pulser 3.

When the moved distance of the echo is represented by y mm, the number n of generated rate pulses during a period Ta has the following relation:

$$n \approx 2y/(\Delta t \cdot S)$$

Accordingly, the data supplied from the ROM 33 to the UP/DOWN counter 35 becomes 8 bit data represented by binary number from the numberic value $(255-n)$. The counter 35 counts up by n with the rate pulse b, with the numeric value $(255-n)$ as an initial value. The Down counter 37 latches the 8 bit data from the UP/DOWN counter 35 every time the counter 37 receives the rate pulse b, down-counts the clock pulse a with the 8 bit data as an intial value, and outputs the signal l when becoming zero. Therefore, the initial value latched by the down counter 37 increases by "1" every time the rate pulse b is renewed such as $(255-n)$ at the first rate pulse, $(255-n+1)$ at the second rate pulse and $(255-n+2)$ at the third rate pulse. Accordingly, the pulse width of the signal l increases in the amount of a period of the clock pulse a every time the rate pulse b is renewed, i.e., at every rate pulse period. When this signal l is inputted to the pulser 3, the timing for driving the transducer 4 can be delayed by a period of the clock pulse a. Since the shifting circuit 21 operates as described above, the Doppler frequency shift fd becomes 500 Hz from the above-described equation (5) when the clock pulse a is 19.2 MHz, the central freqency fc of the ultrasonic wave is 2.4 MHz, the repetition frequency fr $(=1/Tr)$ of the rate pulse b is 4 KHz and the clock pulse a is selected by the multiplexer 41. When the signal selected by the multiplexer 41 is a signal frequency-divided by ½ from the clock pulse a of the ½-frequency divider 39 or a signal frequency-divided by ⅜ from the clock pulse a of the ⅜-frequency divider 40, the Doppler frequency shift fd respectively become 1,000 Hz and 1333 Hz.

In the embodiment described above, the timing for driving the transducer 4 is varied by a predetermined time $\Delta t$ every time the rate pulse b is renewed, but similar effect can also be obtained even if the shifting pulse is applied to the range gate pulse and the range gate pulse is varied by $\Delta t$ at every renewal.

As described above, according to the present invention, the blood flow meter employs a type of detecting the Doppler frequency shift from the actual ultrasonic echo. Accordingly, the present invention provides the ultrasonic pulse Doppler blood flow meter which can readily generally check with the ultrsonic field of the transducer and the receiving circuit.

The present invention is not limited to the particular measurement of the blood flow rate described above. For example, the flow meter of the present invention can also be applied also for a fluid flow rate measuring device of the fluid flowing in a conduit.

What is claimed is:

1. An ultrasonic pulse Doppler blood flow analyzer including a testing circuit comprising:
   rate pulse generating means for producing rate pulses of predetermined periods;
   drive pulse generating means responsive to the rate pulses for producing drive pulses;
   transducer means responsive to the drive pulses for transmitting an ultrasonic waves toward a stationary object to be detected and responsive to the echoes thereof for converting the received echoes into an electrical signal;
   range gate circuit means for producing a range gate pulse after each of the rate pulses for sampling only echo signals from the stationary object;

frequency analyzing means for frequency analyzing the sampled echo signals; and shifting circuit means for shifting the rate pulses and the range gate pulses relative to each other by a predetermined time at every individual period of the rate pulses to change the sampled echo signals into quasi Doppler-shifted signals.

2. The Doppler blood flow meter according to claim 1, wherein said shifting circuit means comprises a counter for counting said rate pulses and producing a repetition signal when a predetermined number corresponding to a predetermined repetition period is counted, an UP/DOWN counter set at the initial value thereof with the repetition signal of said counter for counting said rate pulses and up-counting and down-counting said rate pulses within a period of said repetition period, a memory for storing an initial value to be set, a plurality of frequency dividing means responsive to the said clock signal for frequency-dividing said clock pulse and setting said predetermined time, multiplexer means for selecting any of said dividing means and producing the divided signal, and down counter responsive to said rate pulse for latching the data from said UP/DOWN counter, down-counting the data with the output of said selected dividing means, and producing a signal for driving said drive pulse generating means when the counted data reaches a predetermined value.

3. An ultrasonic pulse Doppler blood flow analyzer including a testing circuit comprising:

rate pulse generating means for producing rate pulses of predetermined repetition periods;

drive pulse generating means responsive to the rate pulses for producing drive pulses;

transducer means responsive to the drive pulses for transmitting ultrasonic waves towards a stationary object to be detected and responsive to the echoes thereof for converting the received echoes into an electrical signal;

range gate circuit means for producing a range gate pulse after each of the rate pulses;

sampling means responsive to the range gate pulses for sampling only echo signals from the stationary object;

frequency analyzing means for frequency analyzing the sampled echo signals;

display means for indicating the intensity of the analyzed signals; and shifting circuit means for shifting the rate pulses relative to the range gate pulses by a predetermined time at every individual period to change the sampled echo signals into quasi Doppler-shifted signals.

4. The Doppler blood flow meter according to claim 3, wherein said shifting circuit means comprises a counter for counting said rate pulses and producing a repetition signal when a predetermined number corresponding to a predetermined repetition period is counted, an UP/DOWN counter set at the initial value thereof with the repetition signal of said counter for counting said rate pulses and up-counting and down-counting said rate pulses within a period of said repetition period, a memory for storing an initial value to be set, a plurality of frequency dividing means responsive to the said clock signal for frequency-dividing said clock pulse and setting said predetermined time, multiplexer means for selecting any of said dividing means and producing the divided signal, and down counter responsive to said rate pulse for latching the data from said UP/DOWN counter, down-counting the data with the output of said selected dividing means, and producing a signal for driving said drive pulse generating means when the counted data reaches a predetermined value.

5. An ultrasonic pulse Doppler blood flow analyzer including a testing circuit comprising:

rate pulse generating means for producing rate pulses of predetermined repetition periods;

drive pulse generating means responsive to the rate pulses for producing drive pulses;

transducer means responsive to the drive pulses for transmitting ultrasonic waves toward a stationary object to be detected and responsive to the echoes thereof for converting the received echoes into an electrical signal;

range gate circuit means for producing a range gate pulse after each of the rate pulses;

sampling means responsive to the range gate pulse for sampling only echo signals from the stationary object;

frequency analyzing means for frequency analyzing the sampled echo signals; and shifting circuit means for shifting the range gate pulses by a predetermined time at every individual period to change the sampled echo signals into quasi Doppler-shifted signals.

* * * * *